(12) United States Patent
Cao et al.

(10) Patent No.: US 11,944,483 B2
(45) Date of Patent: Apr. 2, 2024

(54) RADIATION DETECTOR WITH AUTOMATIC EXPOSURE CONTROL AND A METHOD OF AUTOMATIC EXPOSURE CONTROL

(71) Applicant: SHENZHEN XPECTVISION TECHNOLOGY CO., LTD., Shenzhen (CN)

(72) Inventors: Peiyan Cao, Shenzhen (CN); Yurun Liu, Shenzhen (CN)

(73) Assignee: SHENZHEN XPECTVISION TECHNOLOGY CO., LTD., Shenzhen (CN)

( * ) Notice: Subject to any disclaimer, the term of this patent is extended or adjusted under 35 U.S.C. 154(b) by 241 days.

(21) Appl. No.: 17/178,851

(22) Filed: Feb. 18, 2021

(65) Prior Publication Data
US 2021/0169436 A1 Jun. 10, 2021

Related U.S. Application Data

(63) Continuation of application No. PCT/CN2018/106386, filed on Sep. 19, 2018.

(51) Int. Cl.
| | |
|---|---|
| *A61B 6/00* | (2006.01) |
| *A61B 6/42* | (2024.01) |
| *G01N 23/046* | (2018.01) |
| *G01T 1/02* | (2006.01) |
| *G01T 1/24* | (2006.01) |

(52) U.S. Cl.
CPC ............ *A61B 6/542* (2013.01); *A61B 6/4233* (2013.01); *G01N 23/046* (2013.01); *G01T 1/026* (2013.01); *G01T 1/247* (2013.01); *G01N 2223/419* (2013.01); *G01N 2223/501* (2013.01)

(58) Field of Classification Search
CPC .................. A61B 6/4233; A61B 6/542; G01N 2223/419; G01N 2223/501; G01N 23/046; G01T 1/026; G01T 1/247
See application file for complete search history.

(56) References Cited

U.S. PATENT DOCUMENTS

| | | | | | |
|---|---|---|---|---|---|
| 4,131,797 | A | * | 12/1978 | Franke | ..................... H05G 1/44 378/111 |
| 6,151,383 | A | * | 11/2000 | Xue | ....................... A61B 6/542 378/97 |
| 6,404,851 | B1 | * | 6/2002 | Possin | .................. G01T 1/2928 348/E3.019 |
| 2002/0085672 | A1 | | 7/2002 | Ganin et al. | |
| 2002/0191741 | A1 | * | 12/2002 | Brendler | ................ A61B 6/542 378/96 |

(Continued)

FOREIGN PATENT DOCUMENTS

| | | |
|---|---|---|
| CN | 1484321 A | 3/2004 |
| CN | 103156627 A | 6/2013 |

(Continued)

*Primary Examiner* — Blake C Riddick
(74) *Attorney, Agent, or Firm* — IPRO, PLLC; Qian Gu

(57) ABSTRACT

Disclosed herein is a method comprising: determining doses of radiation received by a first set of pixels of a radiation detector; determining that the doses satisfy a criterion; adjusting exposure of the radiation detector to the radiation in response to the doses satisfying the criterion; and forming an image based on radiation received by a second set of pixels of the radiation detector.

22 Claims, 13 Drawing Sheets

(56) References Cited

U.S. PATENT DOCUMENTS

| | | | |
|---|---|---|---|
| 2004/0096035 A1* | 5/2004 | Yamazaki | A61B 6/4291 378/97 |
| 2005/0169425 A1* | 8/2005 | Takasawa | A61B 6/542 378/97 |
| 2008/0260107 A1* | 10/2008 | Falbo | A61B 6/0442 378/208 |
| 2008/0260108 A1* | 10/2008 | Falbo | A61B 6/0442 378/208 |
| 2011/0249791 A1* | 10/2011 | Wang | A61B 6/547 378/62 |
| 2012/0195408 A1* | 8/2012 | Walk | H05G 1/40 378/165 |
| 2012/0305791 A1* | 12/2012 | Watanabe | G01T 1/247 250/394 |
| 2012/0318986 A1* | 12/2012 | Kanagawa | G01T 1/2928 250/354.1 |
| 2013/0126742 A1* | 5/2013 | Hayun | G01T 1/2018 250/366 |
| 2013/0148782 A1* | 6/2013 | Tajima | A61B 6/548 378/62 |
| 2013/0202086 A1* | 8/2013 | Tsuji | H01L 27/14605 378/62 |
| 2013/0208852 A1* | 8/2013 | Koishi | A61B 6/5288 378/19 |
| 2013/0208860 A1* | 8/2013 | Sugizaki | A61B 6/4233 378/62 |
| 2013/0223592 A1* | 8/2013 | Sato | A61B 6/542 378/97 |
| 2013/0251106 A1* | 9/2013 | Tajima | A61B 6/4233 378/97 |
| 2014/0064448 A1* | 3/2014 | Ito | A61B 6/542 378/97 |
| 2014/0086391 A1* | 3/2014 | Ohta | A61B 6/4233 378/91 |
| 2014/0177798 A1* | 6/2014 | Kitagawa | A61B 6/56 378/62 |
| 2014/0205066 A1* | 7/2014 | Kitagawa | A61B 6/542 378/62 |
| 2015/0030129 A1* | 1/2015 | Tajima | A61B 6/4291 378/62 |
| 2015/0036802 A1 | 2/2015 | Tajima et al. | |
| 2015/0055752 A1* | 2/2015 | Takahashi | H05G 1/30 378/91 |
| 2015/0055753 A1* | 2/2015 | Tajima | A61B 6/4283 378/62 |
| 2015/0078528 A1* | 3/2015 | Okada | G01T 1/15 378/97 |
| 2015/0131784 A1* | 5/2015 | Tajima | G01T 1/1603 378/97 |
| 2015/0139398 A1* | 5/2015 | Tajima | G01T 1/026 378/62 |
| 2015/0164458 A1* | 6/2015 | Tajima | H01L 27/14605 378/97 |
| 2015/0164459 A1* | 6/2015 | Ito | A61B 6/4233 378/97 |
| 2015/0164461 A1* | 6/2015 | Imamura | A61B 6/542 378/97 |
| 2015/0182182 A1* | 7/2015 | Tajima | A61B 6/542 378/189 |
| 2015/0189194 A1* | 7/2015 | Tajima | H04N 5/32 378/62 |
| 2015/0192684 A1* | 7/2015 | Ito | G01T 1/20 250/361 R |
| 2015/0230324 A1* | 8/2015 | Kuwabara | A61B 6/4233 378/108 |
| 2015/0317771 A1* | 11/2015 | Kato | A61B 6/4233 378/62 |
| 2015/0363926 A1* | 12/2015 | Enomoto | A61B 6/545 382/132 |
| 2016/0183908 A1* | 6/2016 | Hayashida | A61B 6/4291 378/207 |
| 2017/0020478 A1* | 1/2017 | Tanaka | A61B 6/542 |
| 2017/0079610 A1* | 3/2017 | Morf | A61B 6/4233 |
| 2017/0202534 A1* | 7/2017 | Crotty | A61B 6/465 |
| 2017/0374295 A1* | 12/2017 | Topfer | H04N 5/361 |
| 2018/0055473 A1* | 3/2018 | Torii | A61B 6/527 |

FOREIGN PATENT DOCUMENTS

| | | |
|---|---|---|
| CN | 103239245 A | 8/2013 |
| CN | 104124256 A | 10/2014 |
| CN | 105030262 A | 11/2015 |
| CN | 106352975 A | 1/2017 |
| EP | 2623032 B1 | 9/2015 |

* cited by examiner

RADIATION DETECTOR WITH AUTOMATIC EXPOSURE CONTROL AND A METHOD OF AUTOMATIC EXPOSURE CONTROL

TECHNICAL FIELD

The disclosure herein relates to radiation detectors, particularly relates to radiation detectors with automatic exposure control.

BACKGROUND

A radiation detector is a device that measures a property of a radiation. Examples of the property may include a spatial distribution of the intensity, phase, and polarization of the radiation. The radiation may be one that has interacted with a subject. For example, the radiation measured by the radiation detector may be a radiation that has penetrated or reflected from the subject. The radiation may be an electromagnetic radiation such as infrared light, visible light, ultraviolet light, X-ray or γ-ray. The radiation may be of other types such as α-rays and β-rays. One type of radiation detectors is based on interaction between the radiation and a semiconductor. For example, a radiation detector of this type may have a semiconductor layer that absorbs the radiation and generate charge carriers (e.g., electrons and holes) and circuitry for detecting the charge carriers.

An automatic exposure control (AEC) device (e.g., a physically thin radiation ionization chamber) may be positioned between a radiation source (e.g., X-ray source) and a radiation detector, and be used to adjust (e.g., terminate, reduce) radiation exposure when a predetermined amount of radiation has been received by the radiation detector. AEC devices may be used to significantly reduce, or eliminate variations in image quality between different images, also to reduce the variation in radiation doses to different sized object (e.g., a patient if used for a medical radiography) cross sections.

SUMMARY

Disclosed herein is a method comprising: determining doses of radiation received by a first set of pixels of a radiation detector; determining that the doses satisfy a criterion; adjusting exposure of the radiation detector to the radiation in response to the doses satisfying the criterion; and forming an image based on radiation received by a second set of pixels of the radiation detector.

According to an embodiment, the second set does not include any member of the first set.

According to an embodiment, the first set is a subset of the second set.

According to an embodiment, the first set of pixels are in a same row or a same column of an array.

According to an embodiment, determining the doses is based on electrical signals generated from the radiation received by the first set of pixels.

According to an embodiment, the criterion is that a statistical characteristic of the doses is above a threshold.

According to an embodiment, the statistical characteristic is a median of the doses.

According to an embodiment, the statistical characteristic is a mean of the doses.

According to an embodiment, the statistical characteristic is a ratio of doses exceeding a limit to the doses received by the first set of pixels.

According to an embodiment, adjusting exposure of the radiation detector to the radiation in response to the doses satisfying the criterion comprises preventing the radiation from reaching the radiation detector.

According to an embodiment, adjusting exposure of the radiation detector to the radiation in response to the doses satisfying the criterion comprises stopping producing the radiation.

According to an embodiment, the first set of pixels are distributed among a set of chips; wherein each chip in the set comprises a subset of pixels of the first set.

According to an embodiment, determining that the doses satisfy a criterion comprises counting a number of subsets whose doses received by the pixels of each of the subsets satisfy a condition; wherein the criterion is that ratio of the number of subsets to the total number of subsets in the plurality is above a threshold.

According to an embodiment, the condition is that a statistical characteristic of the doses received by the pixels of each of the subsets is above another threshold.

Disclosed herein is an apparatus comprising: a radiation source; a radiation detector comprising a processor; wherein the processor is configured: to determine doses of radiation received by a first set of pixels of the radiation detector, to determine that the doses satisfy a criterion, to adjust exposure of the radiation detector to the radiation in response to the doses satisfying the criterion, and to form an image based on radiation received by a second set of pixels of the radiation detector.

According to an embodiment, the second set does not include any member of the first set.

According to an embodiment, the first set is a subset of the second set.

According to an embodiment, the first set of pixels are in a same row or a same column of an array.

According to an embodiment, the criterion is that a statistical characteristic of the doses is above a threshold.

According to an embodiment, the statistical characteristic is a median of the doses.

According to an embodiment, the statistical characteristic is a mean of the doses.

According to an embodiment, the statistical characteristic is a ratio of doses exceeding a limit to the doses received by the first set of pixels.

According to an embodiment, the apparatus further comprises a shutter configured to prevent the radiation from reaching the radiation detector when the processor adjusts exposure of the radiation detector to the radiation in response to the doses satisfying the criterion.

According to an embodiment, the radiation source is configured to stop producing the radiation when the processor adjusts exposure of the radiation detector to the radiation in response to the doses satisfying the criterion.

According to an embodiment, the first set of pixels are distributed among a set of chips; wherein each chip in the set comprises a subset of pixels of the first set.

According to an embodiment, the processor comprises a counter configured to count a number of subsets whose doses received by the pixels of each of the subsets satisfy a condition; wherein the criterion is that ratio of the number of subsets to the total number of subsets in the plurality is above a threshold.

According to an embodiment, the condition is that a statistical characteristic of the doses received by the pixels of each of the subsets is above another threshold.

DETAILED DESCRIPTION

Figure 1A:
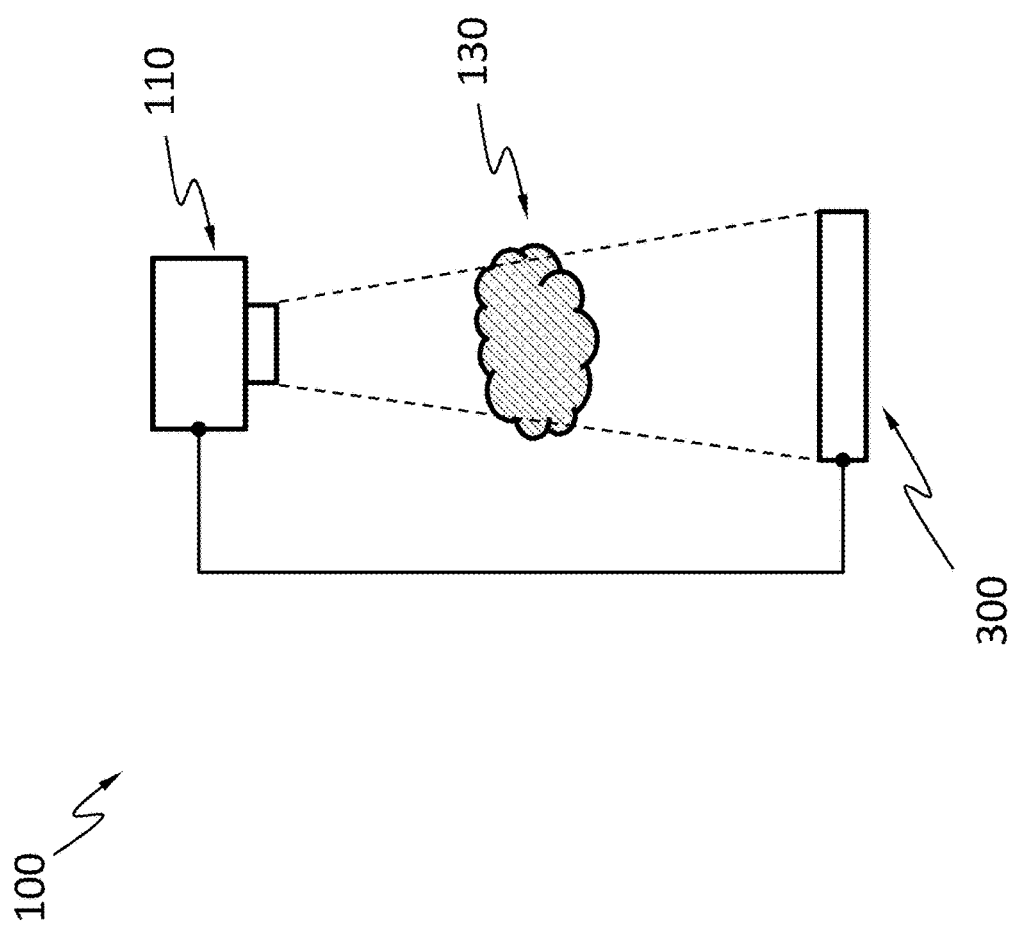
FIG. 1A and FIG. 1B schematically show a system, according to an embodiment.
Figure 1B:
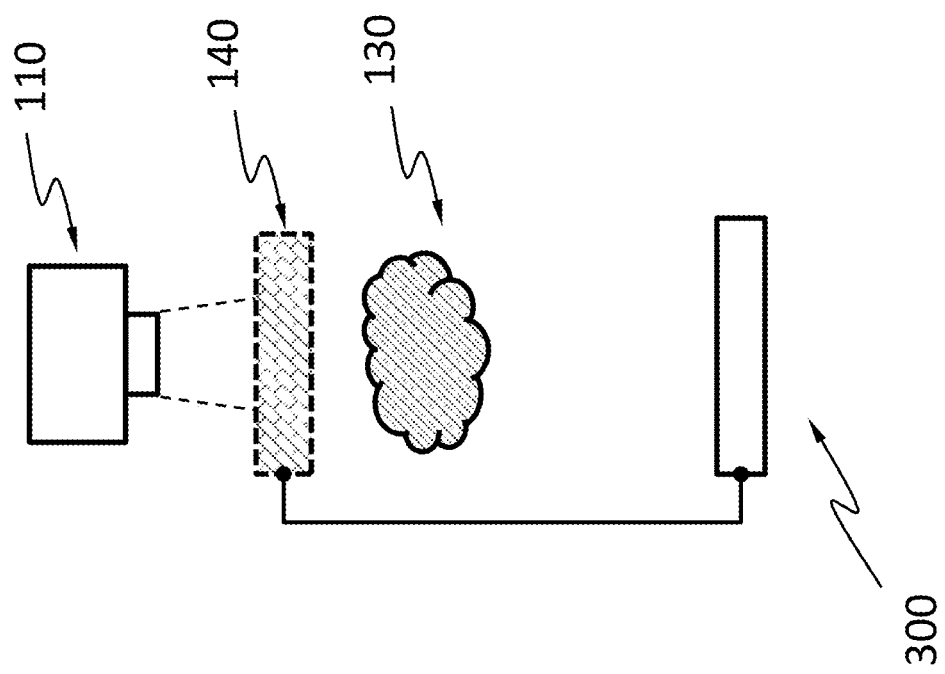

FIG. 1A and FIG. 1B schematically show a system 100, according to an embodiment. The system 100 may have a radiation source 110 and a radiation detector 300. The radiation source 110 may be configured to generate radiation directed through an object 130 toward the radiation detector 300. The radiation detector 300 may detect the radiation from the radiation source 110 and process the signals produced by the radiation to generate an image of the object 130. An image of the object 130 may be a set of position-dependent data (e.g., intensity of the radiation) produced by the radiation detector 300 after processing the radiation incident thereon. The radiation detector 300 may be configured to adjust (e.g., terminate or reduce) exposure of the radiation detector 300 to the radiation from the radiation source 110 when certain criteria are met. For instance, a processor (e.g., processor 322 in FIG. 3A) may measure doses of radiation received by the radiation detector 300 (e.g., doses of radiation transmitted through the object 130), and adjust the exposure (e.g., turn off the radiation source 110 or block the radiation therefrom) when the doses satisfy a criterion. For instance, the radiation source 110 may be controlled by the processor (e.g., processor 322 in FIG. 3A) such that the processor may turn the radiation source 110 off. As shown in the example of FIG. 1B, the system 100 may comprise a shutter 140 configured to prevent the radiation from reaching the radiation detector 300 or the object 130. The processor may control the operation of the shutter 140. The shutter 140 may comprise a material with a high mass attenuation coefficient for the radiation from the radiation source 110.

Figure 2A:
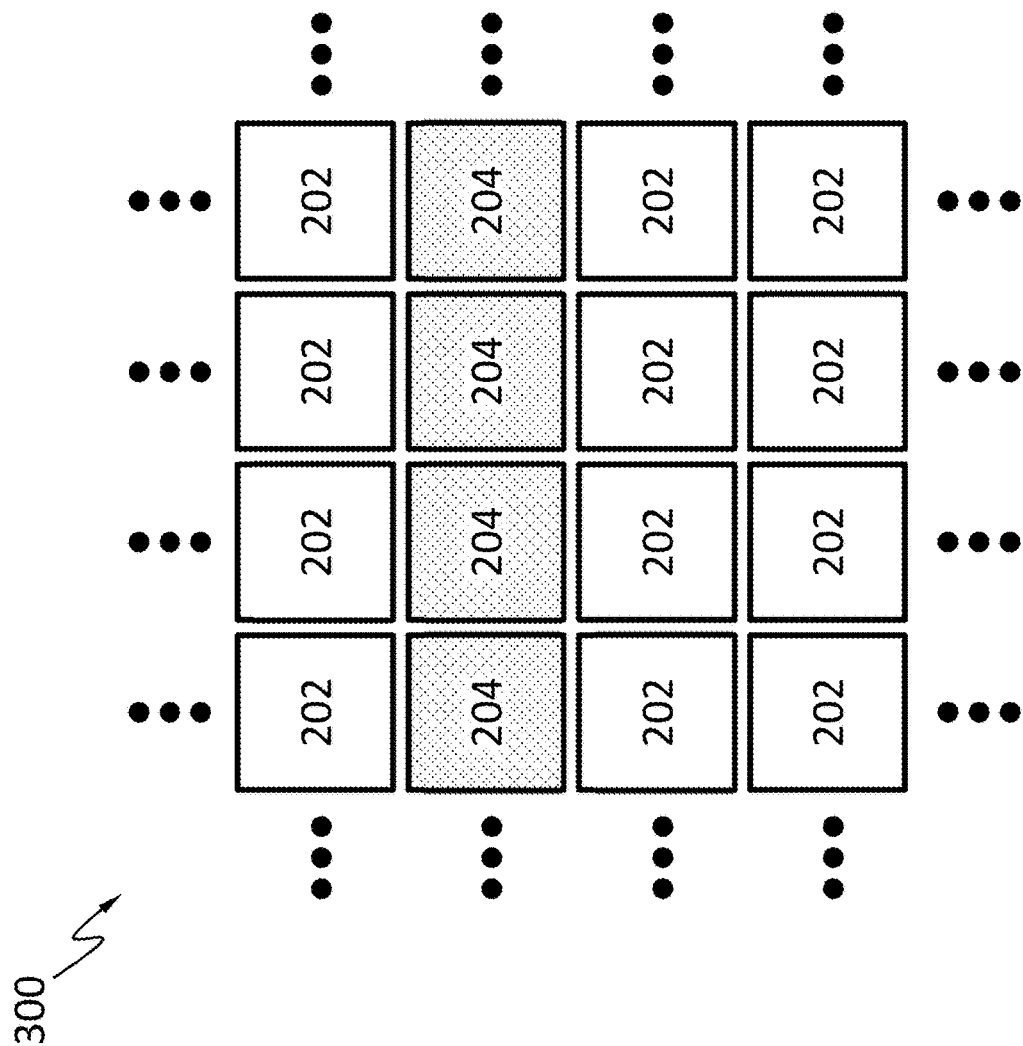
FIG. 2A schematically shows the radiation detector, according to an embodiment.

FIG. 2A schematically shows the radiation detector 300, according to an embodiment. The radiation detector 300 has an array of pixels including a first set of pixels 204 and a second set of pixels 202. Each pixel in the array may be configured to detect radiation from the radiation source 110 incident thereon and may be configured measure a characteristic (e.g., the energy of the particles, the wavelength, and the frequency) of the radiation. For example, each pixel is configured to count numbers of radiation particles incident thereon whose energy falls in a plurality of bins, within a period of time. All the pixels may be configured to count the numbers of radiation particles incident thereon within a plurality of bins of energy within the same period of time. When the incident radiation particles have similar energy, the pixels may be simply configured to count numbers of radiation particles incident thereon within a period of time, without measuring the energy of the individual radiation particles. Each pixel may have its own analog-to-digital converter (ADC) configured to digitize an analog signal representing the energy of an incident radiation particle into a digital signal, or to digitize an analog signal representing the total energy of a plurality of incident radiation particles into a digital signal. The pixels may be configured to operate in parallel. For example, when one pixel measures an incident radiation particle, another pixel may be waiting for a radiation particle to arrive.

The array may be a rectangular array, a honeycomb array, a hexagonal array or any other suitable array. The second set may or may not include any member of the first set. For instance, the first set may be a subset of the second set. The first set of pixels 204 may be in the same row or the same column of the array but is not necessarily so arranged. In the example of FIG. 2A, the first set of pixels 204 are in the same row and no pixel of the first set of pixels 204 belongs to the second set of pixels 202. In an example, the second set of pixels 202 may include some or all of the pixels of the first set of pixels 204, i.e., the first set of pixels 204 being a subset of the second set of pixels 202.

Figure 2B:
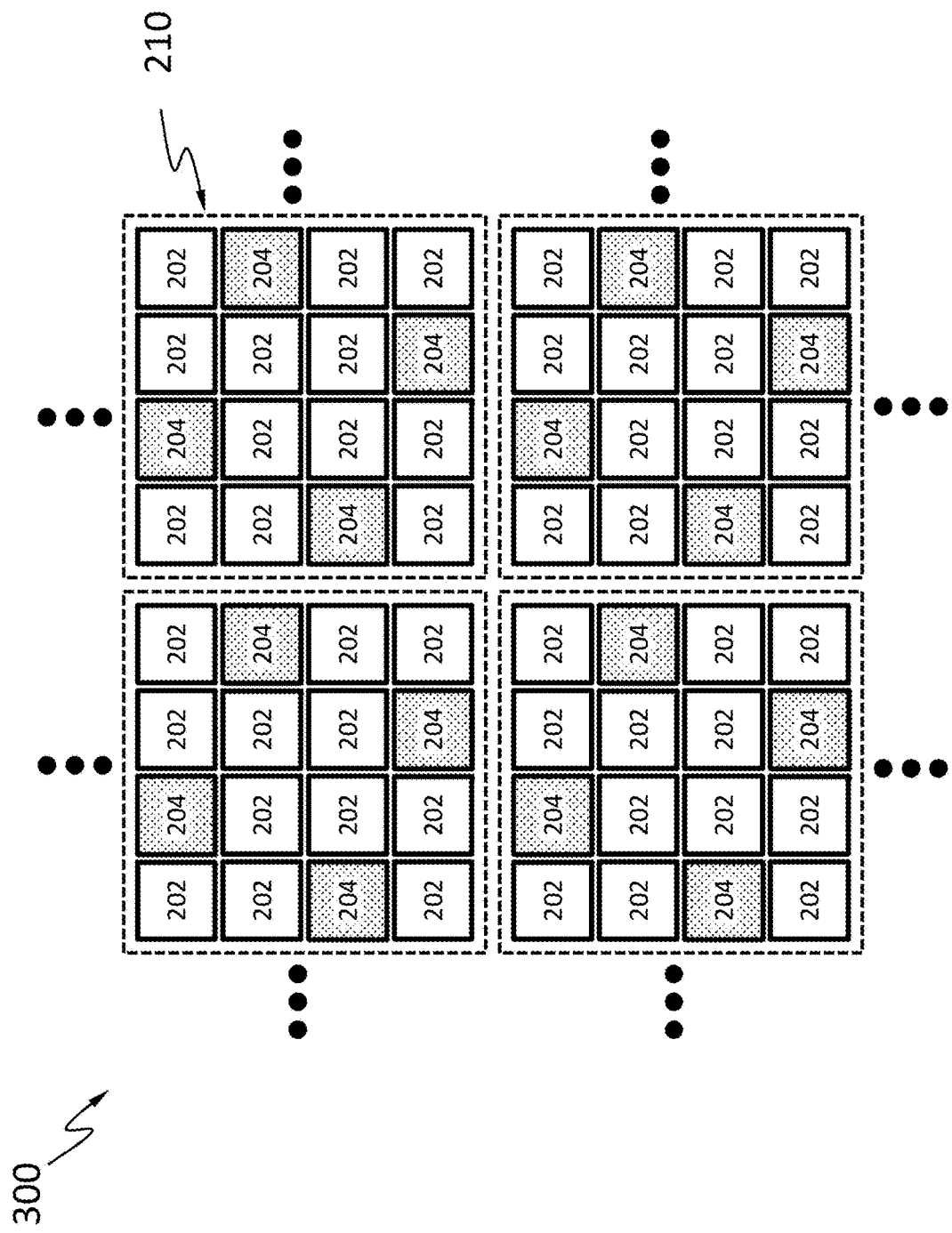
FIG. 2B schematically shows an alternative example of the radiation detector, according to an embodiment.

FIG. 2B schematically shows an alternative example of the radiation detector 300, according to an embodiment. The radiation detector 300 may include a set of chips 210. The first set of pixels 204 may be distributed among the set of chips 210. In other words, each of the chips 210 may comprise a subset of the first set, and each of the subsets may include one or more pixels 204 of the first set. The number and distribution of pixels 204 in one subset is not necessarily the same as that of another subset.

Figure 3A:
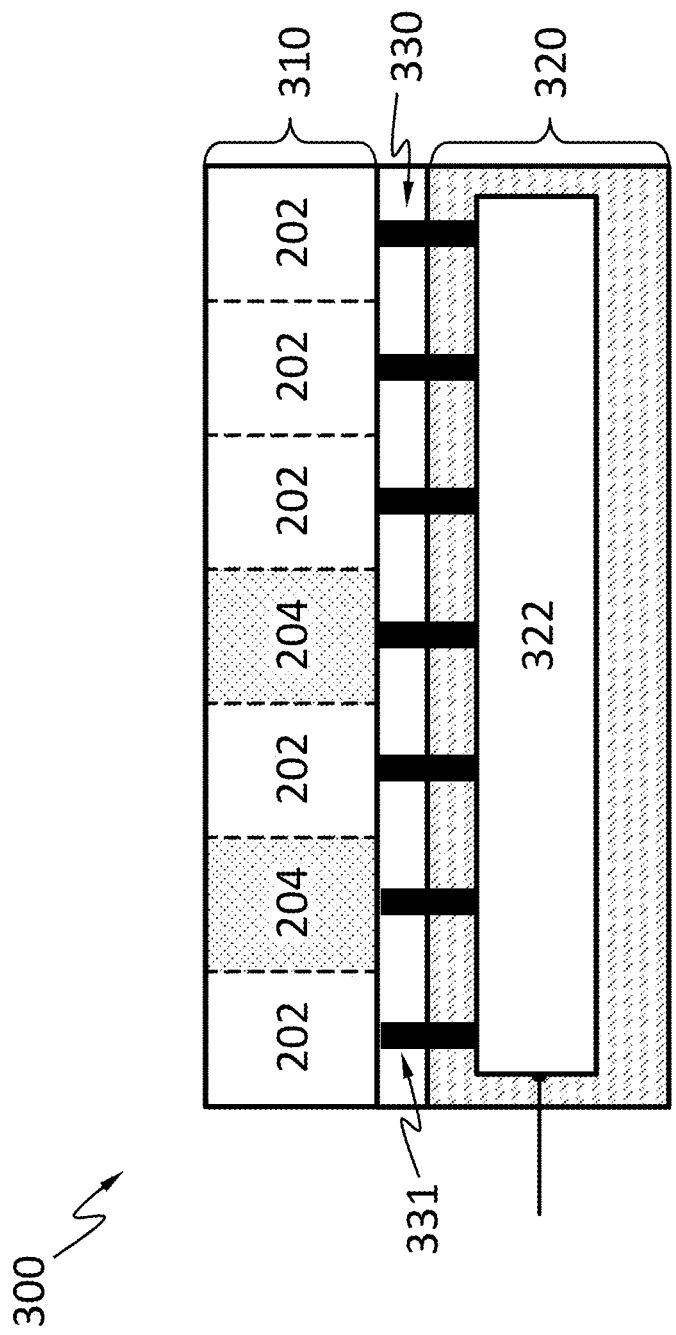
FIG. 3A schematically shows a cross-sectional view of the radiation detector, according to an embodiment.
Figure 4A:
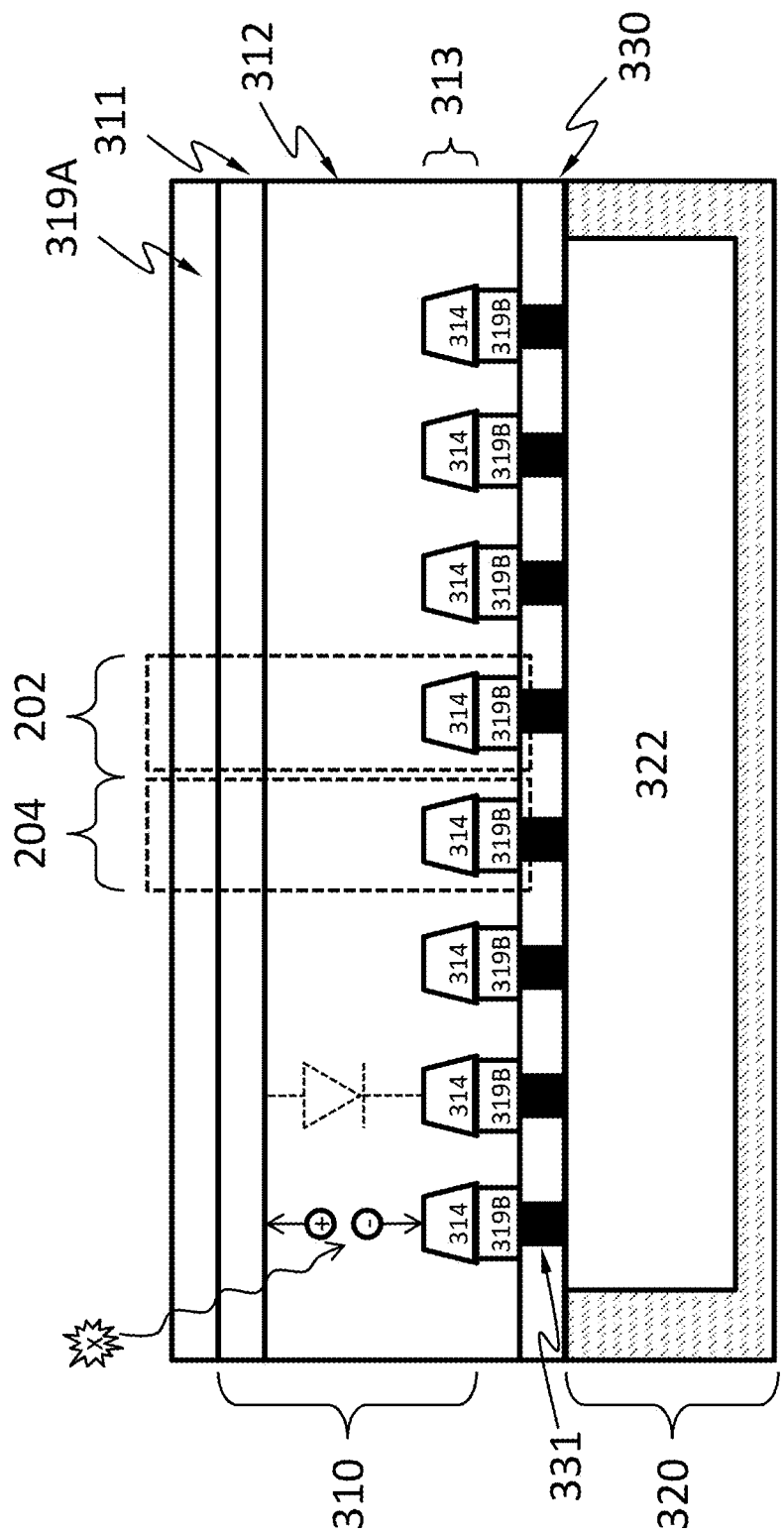
FIG. 4A schematically shows a detailed cross-sectional view of the radiation detector shown in FIG. 3A, according to an embodiment.
Figure 4B:
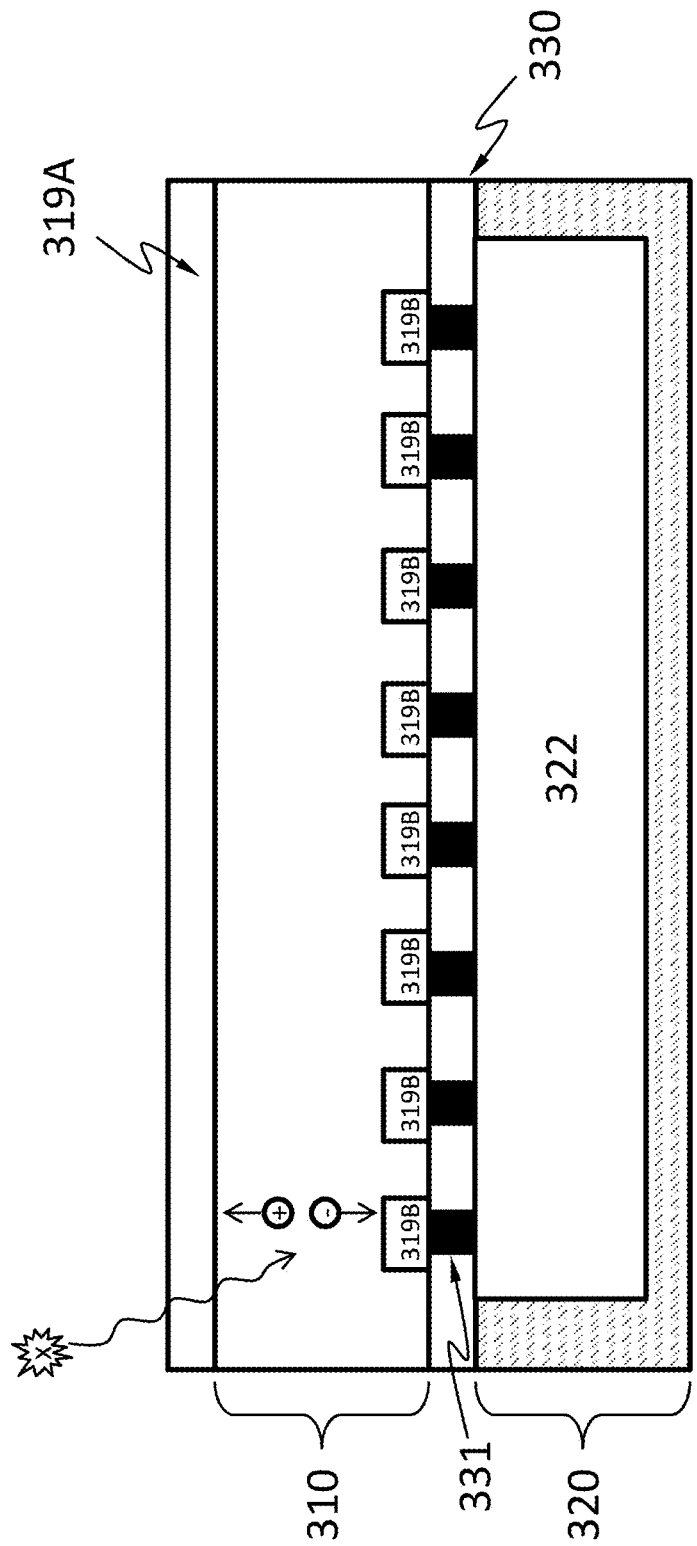
FIG. 4B schematically shows a detailed cross-sectional view of the radiation detector shown in FIG. 3A, according to an embodiment.

FIG. 3A schematically shows a cross-sectional view of the radiation detector 300, according to an embodiment. The radiation detector 300 may comprise a radiation absorption layer 310 and an electronics layer 320 (e.g., an ASIC) for processing or analyzing electrical signals incident radiation generates in the radiation absorption layer 310. The radiation absorption layer 310 may include a semiconductor material such as, silicon, germanium, GaAs, CdTe, CdZnTe, or a combination thereof. The semiconductor may have a high mass attenuation coefficient for the radiation of interest. The radiation absorption layer 310 may include one or more diodes (e.g., p-i-n or p-n) or resistors, as shown in FIG. 4A or FIG. 4B. The radiation detector 300 may or may not include a scintillator.

When the radiation hits the radiation absorption layer 310, it may be absorbed and generate one or more charge carriers by a number of mechanisms. A particle of the radiation may generate 10 to 100000 charge carriers. The charge carriers may drift to the electrical contacts 319A and 319B under an electric field. The field may be an external electric field. The charge carriers may drift in directions such that the charge carriers generated by a single particle of the radiation are not substantially shared by two different pixels (e.g., 204 or 202) ("not substantially shared" here means less than 2%, less than 0.5%, less than 0.1%, or less than 0.01% of these charge carriers flow to a different one of the pixels than the rest of the charge carriers).

The radiation detector 300 may include a processor 322 configured to determine doses of radiation received by the first set of pixels 204 and to adjust exposure of the radiation detector 300 to the radiation, as shown in FIG. 1A and FIG. 1B. The processor 322 may be in the electronics layer 320. In an embodiment, the processor 322 may include an analog circuitry such as a filter network, amplifiers, integrators, and comparators, or a digital circuitry such as microprocessors, and memory. The processor 322 may include one or more ADCs. The processor 322 may include components shared by the pixels or components dedicated to a single pixel. In the case of FIG. 2B, the processor 322 may comprise components shared by the set of chips 210 or components dedicated to a single chip 210. The processor 322 may be electrically connected to the pixels by vias 331. Space among the vias may be filled with a filler material 330, which may increase the mechanical stability of the connection of the electronics layer 320 to the radiation absorption layer 310. Other bonding techniques are possible to connect the processor 322 to the pixels without using vias.

Figure 3B:
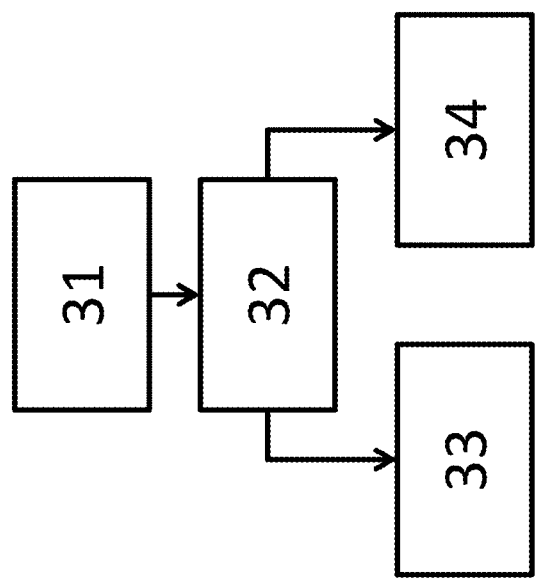
FIG. 3B shows a flow chart for a method suitable for AEC, for example, using the system as shown in FIG. 1A and FIG. 1B.

FIG. 3B shows a flow chart for a method suitable for AEC, for example, using the system 100 as shown in FIG. 1A and FIG. 1B.

In procedure 31, doses of radiation received by the first set of pixels 204 are determined determine, e.g., using the processor 322. In an embodiment, the doses are determined based on electrical signals generated from the radiation received by the first set of pixels 204.

In procedure 32, whether the doses satisfying a criterion is determined, e.g., using the processor 322. The criterion may be that a statistical characteristic of the doses is above a threshold. The value of the threshold may be pre-determined and set based on the specific needs of applications. In an embodiment, the statistical characteristic may be a median of the doses or a mean of the doses. In an embodiment, the statistical characteristic may be a ratio of doses exceeding a limit to the doses received by the first set of pixels 204. For instance, a number of doses that exceed the limit is counted by a counter and used to calculate the ratio. The limit may be a percentage value such as 80%, 90%, 100% or any other suitable value. In the case shown in FIG. 2B, the chips 210 in the set each comprises a subset of the first set, and a number of subsets (i.e., a number of chips 210) whose doses satisfy a condition may be counted by the counter. The condition may be that a statistical characteristic of the doses of a subset is above a threshold. The criterion may be that the ratio of the number of subsets to the total number of subsets in the plurality is above another threshold. For instance, the other threshold may be a percentage value such as 80%, 90%, 100% or any other suitable value.

In procedure 33, exposure of the radiation detector 300 to the radiation is adjusted in response to the doses satisfying the criterion. In an embodiment, the radiation source 110 may stop producing the radiation once the doses satisfy the criterion. For instance, the processor 322 may connect to the radiation source 110 (as shown in FIG. 1A) and send signals to the radiation source 110 when the criterion is met. The radiation source 110 may be automatically turned off after receiving the signals. In an embodiment, the radiation may be physically blocked (e.g., by the shutter 140 as shown in FIG. 1B) once the doses satisfy the criterion. For instance, the processor 322 may connect to the shutter 140, and control the movement of the shutter to prevent the radiation from reaching the radiation detector 300 or the object 130 when the criterion is met.

In procedure 34, an image is formed based on radiation received by the second set of pixels 202 of the radiation detector 300 before the exposure is adjusted above. The image may be a set of position-dependent data generated by the radiation detector 300. The image may be formed based on the doses of radiation transmitted through the object 130 and received by the second set of pixels 202, and may reflect attenuation characteristics (e.g., composition and thickness) of different parts of the object 130. In an embodiment, the signals (e.g., doses of radiation) from the first set of pixels 204 may also be used to generate portions of the image.

FIG. 4A schematically shows a detailed cross-sectional view of the radiation detector 300 shown in FIG. 3A, according to an embodiment. The radiation absorption layer 310 may include one or more diodes (e.g., p-i-n or p-n) formed by a first doped region 311, one or more discrete regions 314 of a second doped region 313, and an electrical contact 319B. The second doped region 313 may be separated from the first doped region 311 by an optional the intrinsic region 312. The discrete regions 314 are separated from one another by the first doped region 311 or the intrinsic region 312. The first doped region 311 and the second doped region 313 have opposite types of doping (e.g., region 311 is p-type and region 313 is n-type, or region 311 is n-type and region 313 is p-type). Each of the discrete regions 314 of the second doped region 313 forms a diode with the first doped region 311 and the optional intrinsic region 312. Namely, the radiation absorption layer 310 has a plurality of diodes having the first doped region 311 as a shared electrode. The first doped region 311 may also have discrete portions. The electrical contact 319B may include discrete portions each of which is in electrical contact with the discrete regions 314.

In an embodiment, charge carriers generated by a particle of radiation incident around the footprint of one of these discrete regions 314 are not substantially shared with another of these discrete regions 314. The portion of the radiation absorption layer 310 associated with a pixel (202 or 204) may an area around the discrete region 314 in which substantially all (more than 98%, more than 99.5%, more than 99.9%, or more than 99.99% of) charge carriers generated by a particle of the radiation incident therein flow to the discrete region 314. Namely, less than 2%, less than 1%, less than 0.1%, or less than 0.01% of these charge carriers flow beyond the pixel (202 or 204) associated with the discrete region 314.

As shown in an alternative detailed cross-sectional view of the radiation detector 300 in FIG. 4B, according to an embodiment, the radiation absorption layer 310 may include a resistor of a semiconductor material such as, silicon, germanium, GaAs, CdTe, CdZnTe, or a combination thereof, but does not include a diode. The semiconductor may have a high mass attenuation coefficient for the radiation of interest.

In an embodiment, the electrical contact 319B includes discrete portions. The charge carriers generated by a particle of radiation incident around the footprint of one of these discrete portions of the electrical contact 319B are not substantially shared with another of these discrete portions of the electrical contact 319B. The portion of the radiation absorption layer 310 associated with a pixel (202 or 204) may an area around the discrete portion in which substantially all (more than 98%, more than 99.5%, more than 99.9% or more than 99.99% of) charge carriers generated by a particle of the radiation incident therein flow to the discrete portion of the electrical contact 319B. Namely, less than 2%, less than 0.5%, less than 0.1%, or less than 0.01% of these charge carriers flow beyond the pixel (202 or 204) associated with the discrete portion of the electrical contact 319B.

Figure 5A:
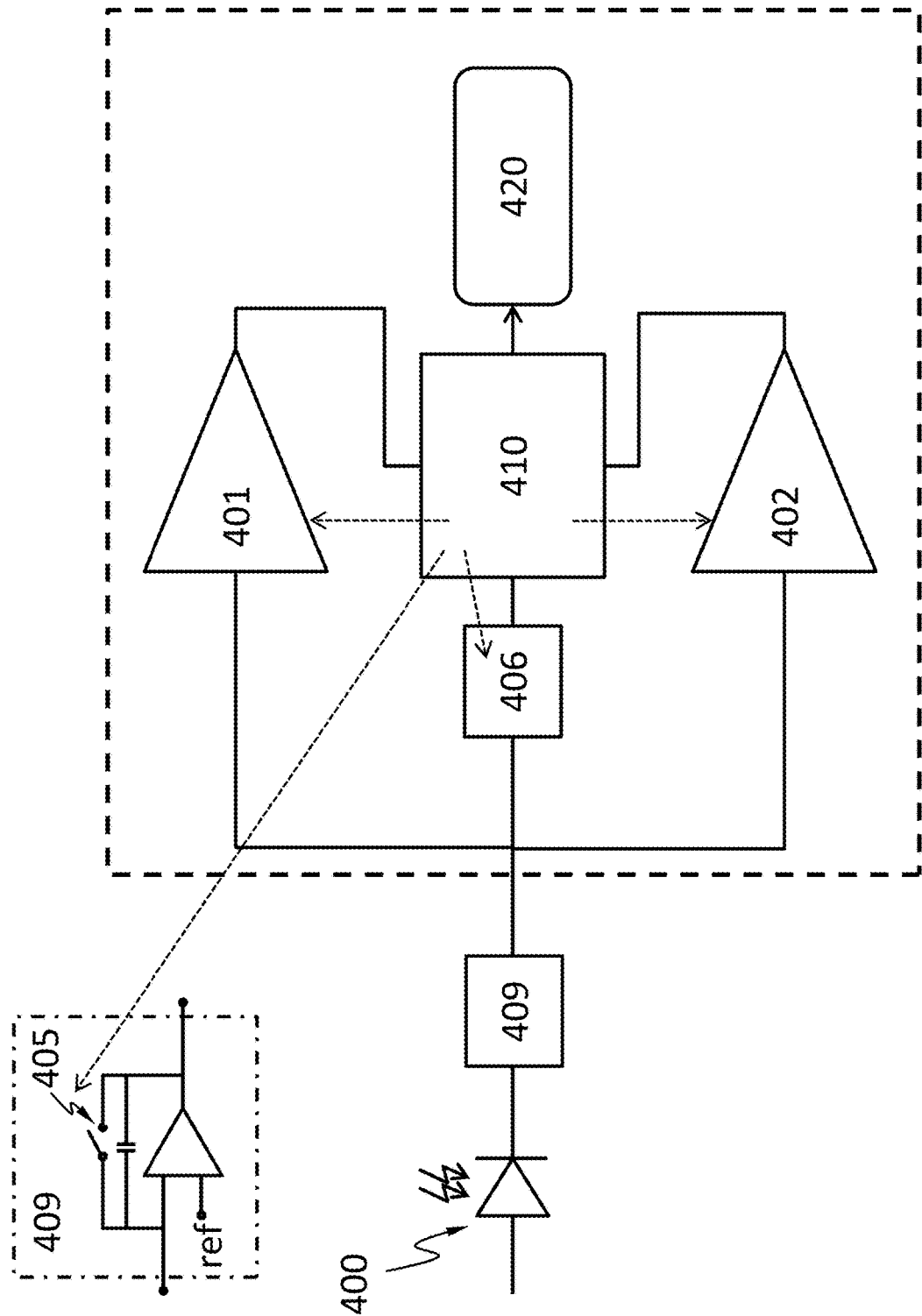
FIG. 5A and FIG. 5B each show a component diagram of a portion of a processor configured to measure doses of radiation, according to an embodiment.
Figure 5B:
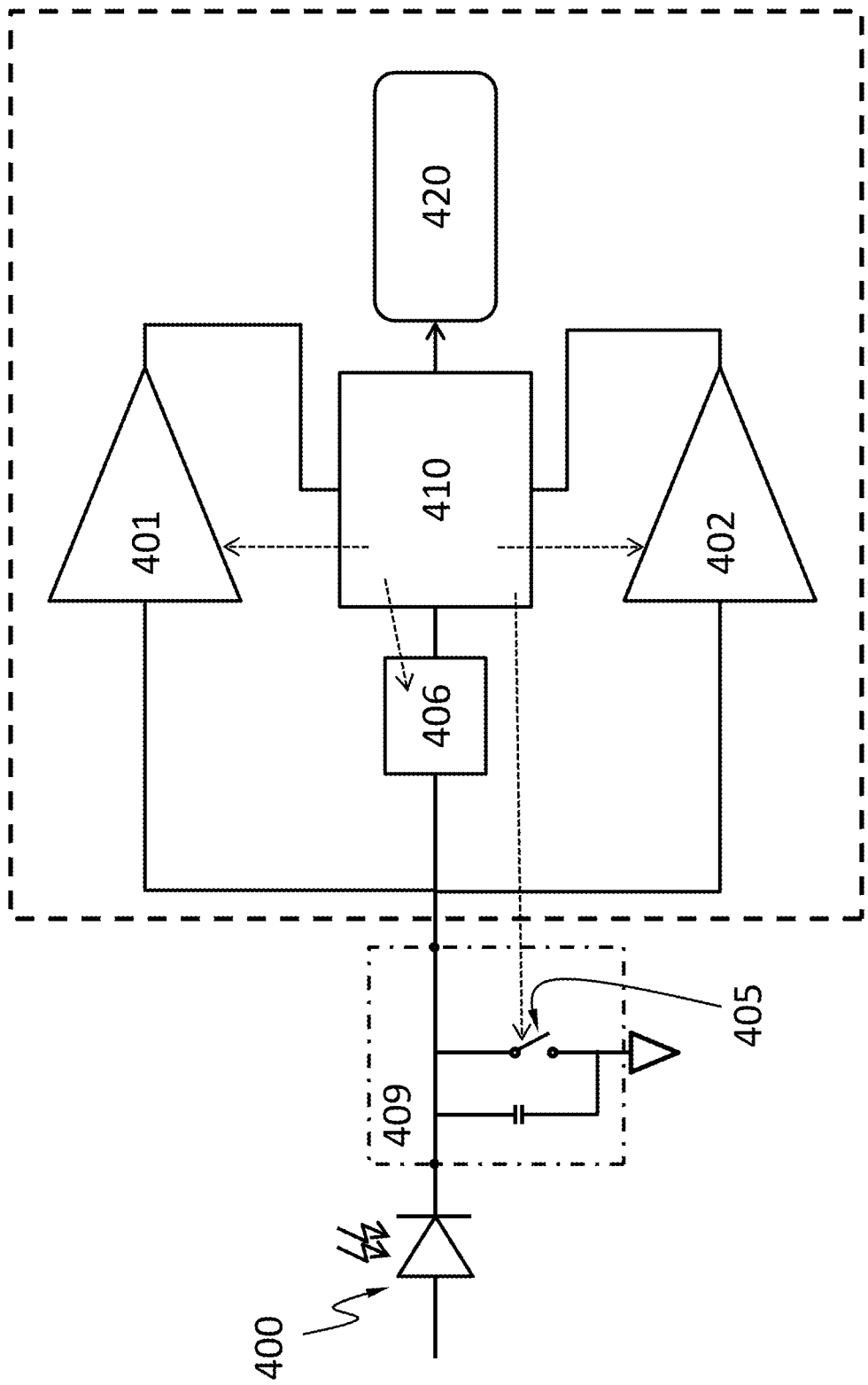

FIG. 5A and FIG. 5B each show a component diagram of a portion of the processor 322 configured to measure doses of radiation, according to an embodiment. The portion of processor 322 includes a capacitor module 409 electrically connected to an electrode of a diode 400 or an electrical contact, wherein the capacitor module is configured to collect charge carriers from the electrode. The capacitor module can include a capacitor and charge carriers from the electrode accumulate on the capacitor over a period of time ("integration period"). After the integration period has expired, the capacitor voltage is sampled and then reset by a reset switch. The capacitor module can include a capacitor directly connected to the electrode. The capacitor may be in the feedback path of an amplifier. The amplifier configured as such is called a capacitive transimpedance amplifier (CTIA). CTIA has high dynamic range by keeping the amplifier from saturating and improves the signal-to-noise ratio by limiting the bandwidth in the signal path.

In addition to the capacitor module 409, the portion of processor 322 may further include a first voltage comparator 401, a second voltage comparator 402, a counter 420, a switch 405, a voltmeter 406 and a controller 410, as shown in FIG. 5A and FIG. 5B.

The first voltage comparator 401 is configured to compare the voltage of an electrode of a diode 400 to a first threshold. The diode may be a diode formed by the first doped region 311, one of the discrete regions 314 of the second doped region 313, and the optional intrinsic region 312. Alternatively, the first voltage comparator 401 is configured to compare the voltage of an electrical contact (e.g., a discrete portion of electrical contact 319B) to a first threshold. The first voltage comparator 401 may be configured to monitor the voltage directly, or calculate the voltage by integrating an electric current flowing through the diode or electrical contact over a period of time. The first voltage comparator 401 may be controllably activated or deactivated by the controller 410. The first voltage comparator 401 may be a continuous comparator. Namely, the first voltage comparator 401 may be configured to be activated continuously, and monitor the voltage continuously. The first voltage comparator 401 configured as a continuous comparator reduces the chance that the portion of processor 322 misses signals generated by an incident radiation particle. The first voltage comparator 401 configured as a continuous comparator is especially suitable when the incident radiation intensity is relatively high. The first voltage comparator 401 may be a clocked comparator, which has the benefit of lower power consumption. The first voltage comparator 401 configured as a clocked comparator may cause the portion of processor 322 to miss signals generated by some incident radiation particles. When the incident radiation intensity is low, the chance of missing an incident radiation particle is low because the time interval between two successive particles is relatively long. Therefore, the first voltage comparator 401 configured as a clocked comparator is especially suitable when the incident radiation intensity is relatively low. The first threshold may be 5-10%, 10%-20%, 20-30%, 30-40% or 40-50% of the maximum voltage one incident radiation particle may generate in the diode or the resistor. The maximum voltage may depend on the energy of the incident radiation particle (i.e., the wavelength of the incident radiation), the material of the radiation absorption layer 310, and other factors. For example, the first threshold may be 50 mV, 100 mV, 150 mV, or 200 mV.

The second voltage comparator 402 is configured to compare the voltage to a second threshold V2. The second voltage comparator 402 may be configured to monitor the voltage directly, or calculate the voltage by integrating an electric current flowing through the diode or the electrical contact over a period of time. The second voltage comparator 402 may be a continuous comparator. The second voltage comparator 402 may be controllably activate or deactivated by the controller 410. When the second voltage comparator 402 is deactivated, the power consumption of the second voltage comparator 402 may be less than 1%, less than 5%, less than 10% or less than 20% of the power consumption when the second voltage comparator 402 is activated. The absolute value of the second threshold is greater than the absolute value of the first threshold. As used herein, the term "absolute value" or "modulus" |x| of a real number x is the non-negative value of x without regard to its sign. Namely, $$|x| = \begin{cases} x, \text{ if } x \geq 0 \\ -x, \text{ if } x \leq 0. \end{cases}$$

The second threshold may be 200%-300% of the first threshold. The second threshold may be at least 50% of the maximum voltage one incident radiation particle may generate in the diode or resistor. For example, the second threshold may be 100 mV, 150 mV, 200 mV, 250 mV or 300 mV. The second voltage comparator 402 and the first voltage comparator 401 may be the same component. Namely, the portion of processor 322 may have one voltage comparator that can compare a voltage with two different thresholds at different times.

The first voltage comparator 401 or the second voltage comparator 402 may include one or more op-amps or any other suitable circuitry. The first voltage comparator 401 or the second voltage comparator 402 may have a high speed to allow the portion of processor 322 to operate under a high flux of incident radiation. However, having a high speed is often at the cost of power consumption.

The counter 420 is configured to register a number of radiation particles reaching the diode or resistor. The number of radiation particles counted is considered a dose of radiation received by a pixel (202 or 204). In an embodiment, the counter 420 is further configured to count the number of doses that exceed the limit or a number of subsets whose doses satisfy the condition as in procedure 32 of FIG. 3B. The counter 420 may count and register a plurality of numbers at the same time. The counter 420 may be a software component (e.g., a number stored in a computer memory) or a hardware component (e.g., a 4017 IC and a 7490 IC).

The controller 410 may be a hardware component such as a microcontroller and a microprocessor. The controller 410 is configured to start a time delay from a time at which the first voltage comparator 401 determines that the absolute value of the voltage equals or exceeds the absolute value of the first threshold (e.g., the absolute value of the voltage increases from below the absolute value of the first threshold to a value equal to or above the absolute value of the first threshold). The absolute value is used here because the voltage may be negative or positive, depending on whether the voltage of the cathode or the anode of the diode or which electrical contact is used. The controller 410 may be configured to keep deactivated the second voltage comparator 402, the counter 420 and any other circuits the operation of the first voltage comparator 401 does not require, before the time at which the first voltage comparator 401 determines that the absolute value of the voltage equals or exceeds the absolute value of the first threshold. The time delay may expire before or after the voltage becomes stable, i.e., the rate of change of the voltage is substantially zero. The phase "the rate of change of the voltage is substantially zero" means that temporal change of the voltage is less than 0.1%/ns. The phase "the rate of change of the voltage is substantially non-zero" means that temporal change of the voltage is at least 0.1%/ns.

The controller 410 may be configured to activate the second voltage comparator during (including the beginning and the expiration) the time delay. In an embodiment, the controller 410 is configured to activate the second voltage comparator at the beginning of the time delay. The term "activate" means causing the component to enter an operational state (e.g., by sending a signal such as a voltage pulse or a logic level, by providing power, etc.). The term "deactivate" means causing the component to enter a non-operational state (e.g., by sending a signal such as a voltage pulse or a logic level, by cut off power, etc.). The operational state may have higher power consumption (e.g., 10 times higher, 100 times higher, 1000 times higher) than the non-operational state. The controller 410 itself may be deactivated until the output of the first voltage comparator 401 activates the controller 410 when the absolute value of the voltage equals or exceeds the absolute value of the first threshold.

The controller 410 may be configured to cause the number registered by the counter 420 to increase by one, if, during the time delay, the second voltage comparator 402 determines that the absolute value of the voltage equals or exceeds the absolute value of the second threshold.

The controller 410 may be configured to cause the voltmeter 406 to measure the voltage upon expiration of the time delay. The controller 410 may be configured to connect the electrode to an electrical ground, so as to reset the voltage and discharge any charge carriers accumulated on the electrode. In an embodiment, the electrode is connected to an electrical ground after the expiration of the time delay. In an embodiment, the electrode is connected to an electrical ground for a finite reset time period. The controller 410 may connect the electrode to the electrical ground by controlling the switch 405. The switch may be a transistor such as a field-effect transistor (FET).

In an embodiment, the portion of processor 322 has no analog filter network (e.g., a RC network).

In an embodiment, the portion of processor 322 has no analog circuitry.

Figure 6:
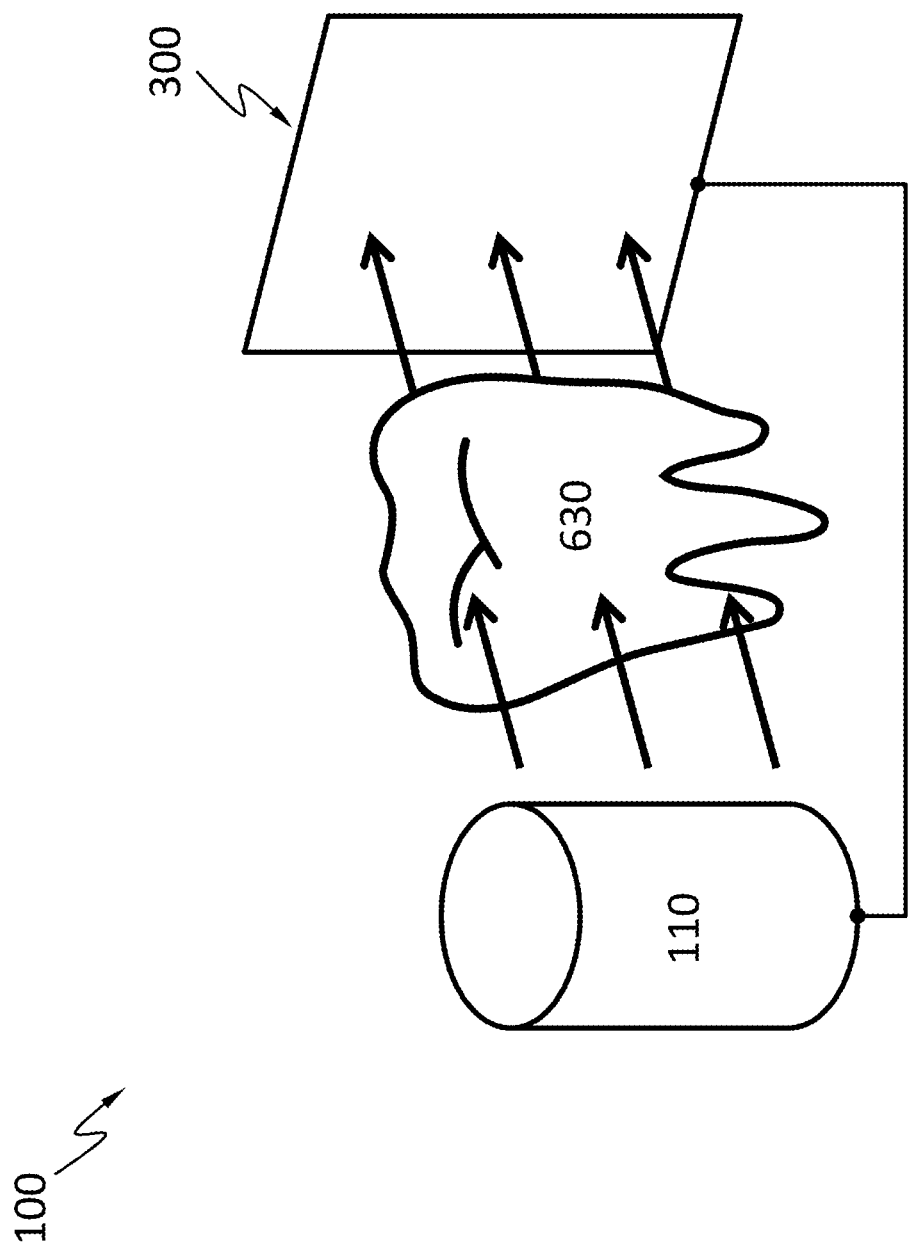
FIG. 6 schematically shows the system 100 described herein being used for medical imaging such as dental X-ray radiography.

The voltmeter 406 may feed the voltage it measures to the controller 410 as an analog or digital signal FIG. 6 schematically shows the system 100 described herein being used for medical imaging such as dental X-ray radiography. The radiation source 110 is an X-ray source. X-ray emitted from the X-ray source penetrates an object 630 that is part of a mammal (e.g., human) mouth. The object 630 may include a maxilla bone, a palate bone, a tooth, the mandible, or the tongue. The X-ray is attenuated by different degrees by the different structures of the object 630 and is projected to the radiation detector 300. The radiation detector 300 forms an image by detecting the intensity distribution of the X-ray and automatically control X-ray exposure of the object 630. Teeth absorb X-ray more than dental caries, infections, periodontal ligament. The dosage of X-ray radiation received by a dental patient is typically small (around 0.150 mSv for a full mouth series).

Figure 7:
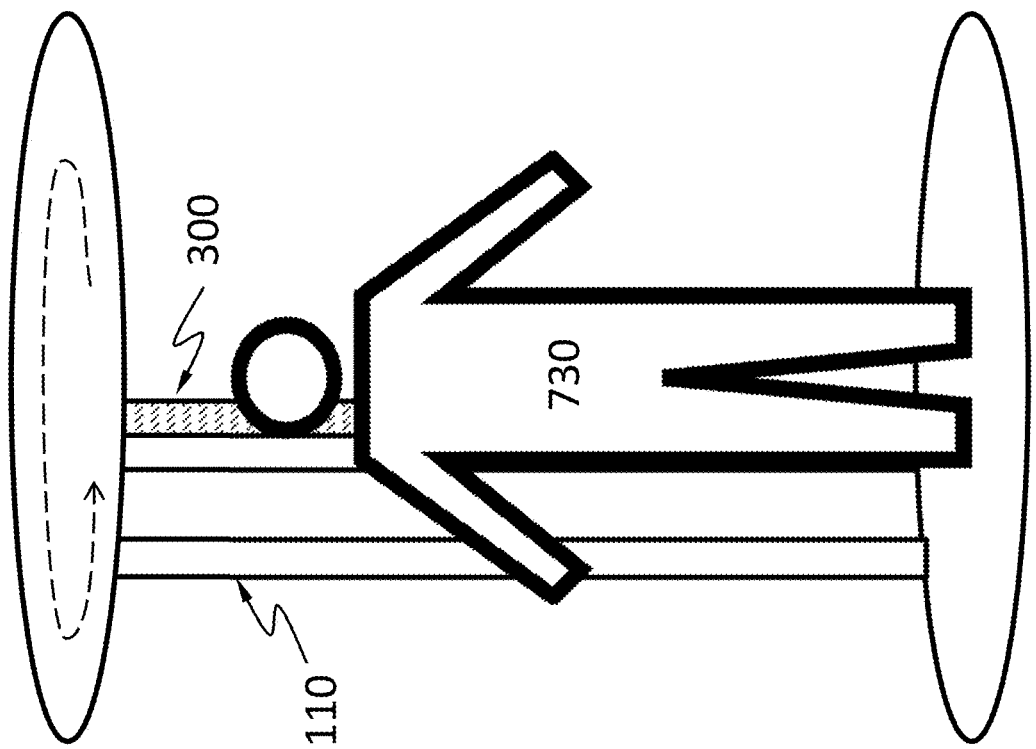
FIG. 7 schematically shows a full-body scanner system comprising the system 100 described herein.

FIG. 7 schematically shows a full-body scanner system comprising the system 100 described herein. The full-body scanner system may detect objects on a person's body for security screening purposes, without physically removing clothes or making physical contact. The full-body scanner system may be able to detect non-metal objects. The radiation source 110 is an X-ray source. X-ray emitted from the X-ray source may backscatter from a human 730 being screened and objects thereon, and be projected to the radiation detector 300. The objects and the human body may backscatter X-ray differently. The radiation detector 300 forms an image by detecting the intensity distribution of the backscattered X-ray, and automatically control X-ray exposure of the human 730. The radiation detector 300 and the X-ray source may be configured to scan the human in a linear or rotational direction.

Figure 8:
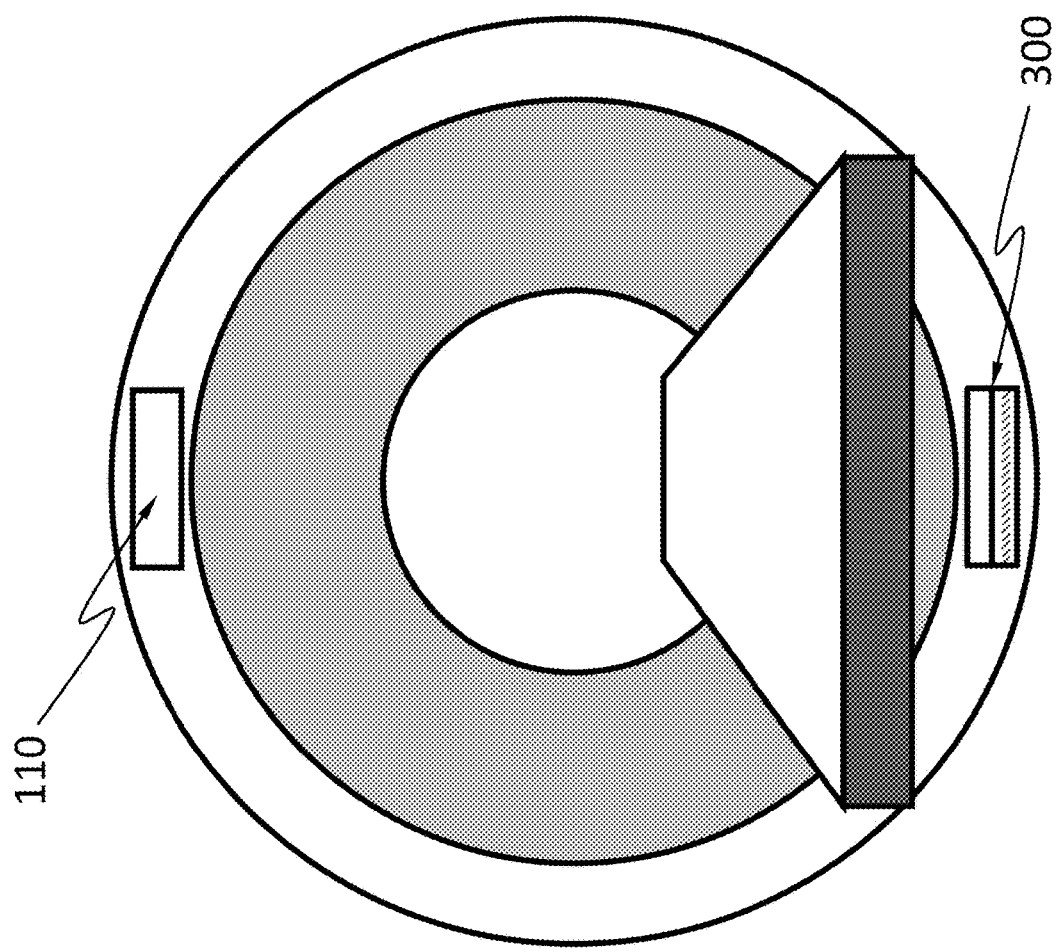
FIG. 8 schematically shows an X-ray computed tomography (X-ray CT) system comprising the system 100 described herein.

FIG. 8 schematically shows an X-ray computed tomography (X-ray CT) system. The X-ray CT system uses computer-processed X-rays to produce tomographic images (virtual "slices") of specific areas of a scanned object. The tomographic images may be used for diagnostic and therapeutic purposes in various medical disciplines, or for flaw detection, failure analysis, metrology, assembly analysis and reverse engineering. The X-ray CT system comprises the system 100 described herein. The radiation source 110 is an X-ray source. The radiation detector 300 and the X-ray source may be configured to rotate synchronously along one or more circular or spiral paths.

The system 100 described here may have other applications such as in an X-ray telescope, X-ray mammography, industrial X-ray defect detection, X-ray microscopy or microradiography, X-ray casting inspection, X-ray non-destructive testing, X-ray weld inspection, X-ray digital subtraction angiography, etc. It may be suitable to use this system 100 in place of a photographic plate, a photographic film, a PSP plate, an X-ray image intensifier, a scintillator, or another semiconductor X-ray detector.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method comprising:
    determining doses of radiation received by a first set of pixels of a radiation detector, based on electrical signals generated from the radiation received by the first set of pixels;
    determining that the doses satisfy a criterion;
    adjusting exposure of the radiation detector to the radiation in response to the doses satisfying the criterion; and
    forming an image based on radiation received by a second set of pixels of the radiation detector;
    wherein the first set is a subset of the second set;
    wherein a set of picture elements of the image are respectively formed using the electrical signals generated from the radiation received by the first set of pixels.

2. The method of claim 1, wherein the first set of pixels are in a same row or a same column of an array.

3. The method of claim 1, wherein the criterion is that a statistical characteristic of the doses is above a threshold.

4. The method of claim 3, wherein the statistical characteristic is a median of the doses.

5. The method of claim 3, wherein the statistical characteristic is a mean of the doses.

6. The method of claim 3, wherein the statistical characteristic is a ratio of doses exceeding a limit to the doses received by the first set of pixels.

7. The method of claim 1, wherein adjusting exposure of the radiation detector to the radiation in response to the doses satisfying the criterion comprises preventing the radiation from reaching the radiation detector.

8. The method of claim 1, wherein adjusting exposure of the radiation detector to the radiation in response to the doses satisfying the criterion comprises stopping producing the radiation.

9. The method of claim 1, wherein the first set of pixels are distributed among a set of chips; wherein each chip in the set comprises a subset of pixels of the first set.

10. The method of claim 9, wherein determining that the doses satisfy a criterion comprises counting a number of subsets whose doses received by the pixels of each of the subsets satisfy a condition; wherein the criterion is that ratio of the number of subsets to the total number of subsets in the plurality is above a threshold.

11. The method of claim 10, wherein the condition is that a statistical characteristic of the doses received by the pixels of each of the subsets is above another threshold.

12. An apparatus comprising:
a radiation source;
a radiation detector comprising a processor;
wherein the processor is configured:
to determine doses of radiation received by a first set of pixels of the radiation detector, based on electrical signals generated from the radiation received by the first set of pixels,
to determine that the doses satisfy a criterion,
to adjust exposure of the radiation detector to the radiation in response to the doses satisfying the criterion, and
to form an image based on radiation received by a second set of pixels of the radiation detector;
wherein the first set is a subset of the second set;
wherein a set of picture elements of the image are respectively formed using the electrical signals generated from the radiation received by the first set of pixels.

13. The apparatus of claim 12, wherein the first set of pixels are in a same row or a same column of an array.

14. The apparatus of claim 12, wherein the criterion is that a statistical characteristic of the doses is above a threshold.

15. The apparatus of claim 14, wherein the statistical characteristic is a median of the doses.

16. The apparatus of claim 14, wherein the statistical characteristic is a mean of the doses.

17. The apparatus of claim 14, wherein the statistical characteristic is a ratio of doses exceeding a limit to the doses received by the first set of pixels.

18. The apparatus of claim 12, further comprising a shutter configured to prevent the radiation from reaching the radiation detector when the processor adjusts exposure of the radiation detector to the radiation in response to the doses satisfying the criterion.

19. The apparatus of claim 12, wherein the radiation source is configured to stop producing the radiation when the processor adjusts exposure of the radiation detector to the radiation in response to the doses satisfying the criterion.

20. The apparatus of claim 12, wherein the first set of pixels are distributed among a set of chips; wherein each chip in the set comprises a subset of pixels of the first set.

21. The apparatus of claim 20, wherein the processor comprises a counter configured to count a number of subsets whose doses received by the pixels of each of the subsets satisfy a condition; wherein the criterion is that ratio of the number of subsets to the total number of subsets in the plurality is above a threshold.

22. The apparatus of claim 21, wherein the condition is that a statistical characteristic of the doses received by the pixels of each of the subsets is above another threshold.

* * * * *